United States Patent
Kingsley et al.

(10) Patent No.: US 12,185,964 B2
(45) Date of Patent: Jan. 7, 2025

(54) END EFFECTOR ASSEMBLIES FOR SURGICAL INSTRUMENTS SUCH AS FOR USE IN ROBOTIC SURGICAL SYSTEMS

(71) Applicant: Covidien LP, Mansfield, MA (US)

(72) Inventors: Dylan R. Kingsley, Broomfield, CO (US); Jason G. Weihe, Longmont, CO (US); William R. Whitney, Boulder, CO (US); Zachary S. Heiliger, Nederland, CO (US); Curtis M. Siebenaller, Frederick, CO (US); Crystal A. Adams, Westminster, CO (US)

(73) Assignee: Covidien LP, Mansfield, MA (US)

( * ) Notice: Subject to any disclaimer, the term of this patent is extended or adjusted under 35 U.S.C. 154(b) by 503 days.

(21) Appl. No.: 17/017,604

(22) Filed: Sep. 10, 2020

(65) Prior Publication Data

US 2022/0071651 A1    Mar. 10, 2022

(51) Int. Cl.
*A61B 17/295* (2006.01)
*A61B 17/29* (2006.01)
(Continued)

(52) U.S. Cl.
CPC .... *A61B 17/295* (2013.01); *A61B 2017/2936* (2013.01); *A61B 2017/320094* (2017.08);
(Continued)

(58) Field of Classification Search
CPC .......... A61B 2017/2936; A61B 17/295; A61B 2034/305
See application file for complete search history.

(56) References Cited

U.S. PATENT DOCUMENTS

| | | |
|---|---|---|
| 702,472 A | 6/1902 | Pignolet |
| 2,801,633 A | 8/1957 | Ehrlich |

(Continued)

FOREIGN PATENT DOCUMENTS

| | | |
|---|---|---|
| EP | 2294998 A1 | 3/2011 |
| EP | 3689282 A1 | 8/2020 |
| WO | 2016045044 A1 | 3/2016 |

OTHER PUBLICATIONS

International Search Report and Written Opinion issued in corresponding International Application No. PCT/US2021/046684 mailed Nov. 30, 2021, 13 pages.

*Primary Examiner* — Joseph A Stoklosa
*Assistant Examiner* — Annie L Shoulders

(57) ABSTRACT

An end effector assembly includes a clevis having first and second spaced-apart arms, a ceiling, a floor, pivot and cam pins extending between the arms, and first and second jaw members. Each jaw member includes a proximal portion and a distal body extending distally from the clevis. The proximal portion of the first jaw member includes a first flag disposed between the first and second arms of the clevis, operably coupled to both the pivot pin and the cam pin, extending vertically at least partially through openings defined within the ceiling and floor. The proximal portion of the second jaw member includes second and third flags disposed between the first and second arms of the clevis in spaced-apart relative to one another and between the ceiling and the floor. The second and third flags are fixedly engaged to the clevis.

20 Claims, 10 Drawing Sheets

(51) Int. Cl.
  *A61B 17/32*  (2006.01)
  *A61B 34/30*  (2016.01)
  *A61B 18/00*  (2006.01)
  *A61B 18/08*  (2006.01)
  *A61B 18/14*  (2006.01)
  *A61B 18/18*  (2006.01)
  *A61B 34/00*  (2016.01)
  *A61B 34/35*  (2016.01)

(52) U.S. Cl.
  CPC ........... *A61B 2018/00077* (2013.01); *A61B 2018/0063* (2013.01); *A61B 18/085* (2013.01); *A61B 18/1445* (2013.01); *A61B 2018/1807* (2013.01); *A61B 2018/1861* (2013.01); *A61B 34/35* (2016.02); *A61B 34/71* (2016.02)

(56) References Cited

U.S. PATENT DOCUMENTS

| | | | |
|---|---|---|---|
| D249,549 | S | 9/1978 | Pike |
| D263,020 | S | 2/1982 | Rau, III |
| D295,893 | S | 5/1988 | Sharkany et al. |
| D295,894 | S | 5/1988 | Sharkany et al. |
| D298,353 | S | 11/1988 | Manno |
| 4,793,218 | A | 12/1988 | Jordan et al. |
| D299,413 | S | 1/1989 | DeCarolis |
| 5,100,506 | A | 3/1992 | Sturtevant et al. |
| 5,242,456 | A | 9/1993 | Nash et al. |
| D343,453 | S | 1/1994 | Noda |
| 5,275,614 | A * | 1/1994 | Haber .......... A61B 17/0469 606/208 |
| 5,302,234 | A | 4/1994 | Grace et al. |
| 5,317,938 | A | 6/1994 | de Juan, Jr. et al. |
| D348,930 | S | 7/1994 | Olson |
| D349,341 | S | 8/1994 | Lichtman et al. |
| D354,564 | S | 1/1995 | Medema |
| 5,383,471 | A | 1/1995 | Funnell |
| 5,395,364 | A | 3/1995 | Anderhub et al. |
| D358,887 | S | 5/1995 | Feinberg |
| 5,431,667 | A | 7/1995 | Thompson et al. |
| 5,486,185 | A | 1/1996 | Freitas et al. |
| 5,486,189 | A | 1/1996 | Mudry et al. |
| 5,522,830 | A | 6/1996 | Aranyi |
| 5,522,839 | A | 6/1996 | Pilling |
| 5,539,973 | A | 7/1996 | Smith et al. |
| 5,571,129 | A | 11/1996 | Porter |
| 5,620,447 | A | 4/1997 | Smith et al. |
| 5,626,609 | A | 5/1997 | Zvenyatsky et al. |
| D384,413 | S | 9/1997 | Zlock et al. |
| 5,707,392 | A | 1/1998 | Kortenbach |
| 5,716,374 | A | 2/1998 | Francese et al. |
| 5,752,973 | A | 5/1998 | Kieturakis |
| H1745 | H | 8/1998 | Paraschac |
| 5,792,135 | A | 8/1998 | Madhani et al. |
| 5,833,692 | A | 11/1998 | Cesarini et al. |
| D402,028 | S | 12/1998 | Grimm et al. |
| 5,848,986 | A | 12/1998 | Lundquist et al. |
| D408,018 | S | 4/1999 | McNaughton |
| D416,089 | S | 11/1999 | Barton et al. |
| 6,013,028 | A | 1/2000 | Jho et al. |
| D424,694 | S | 5/2000 | Tetzlaff et al. |
| D425,201 | S | 5/2000 | Tetzlaff et al. |
| 6,117,158 | A | 9/2000 | Measamer et al. |
| H1904 | H | 10/2000 | Yates et al. |
| 6,202,465 | B1 | 3/2001 | Jankoski et al. |
| 6,277,117 | B1 | 8/2001 | Tetzlaff et al. |
| D449,886 | S | 10/2001 | Tetzlaff et al. |
| D453,923 | S | 2/2002 | Olson |
| D454,951 | S | 3/2002 | Bon |
| D457,958 | S | 5/2002 | Dycus et al. |
| D457,959 | S | 5/2002 | Tetzlaff et al. |
| H2037 | H | 7/2002 | Yates et al. |
| D465,281 | S | 11/2002 | Lang |
| D466,209 | S | 11/2002 | Bon |
| D493,888 | S | 8/2004 | Reschke |
| D496,997 | S | 10/2004 | Dycus et al. |
| D499,181 | S | 11/2004 | Dycus et al. |
| 6,817,974 | B2 | 11/2004 | Cooper et al. |
| D502,994 | S | 3/2005 | Blake, III |
| D509,297 | S | 9/2005 | Wells |
| D525,361 | S | 7/2006 | Hushka |
| 7,101,371 | B2 | 9/2006 | Dycus et al. |
| D531,311 | S | 10/2006 | Guerra et al. |
| 7,122,035 | B2 | 10/2006 | Canady |
| D533,274 | S | 12/2006 | Visconti et al. |
| D533,942 | S | 12/2006 | Kerr et al. |
| D535,027 | S | 1/2007 | James et al. |
| D538,932 | S | 3/2007 | Malik |
| 7,186,261 | B2 | 3/2007 | Prestel |
| D541,418 | S | 4/2007 | Schechter et al. |
| D541,611 | S | 5/2007 | Aglassinge |
| D541,938 | S | 5/2007 | Kerr et al. |
| D545,432 | S | 6/2007 | Watanabe |
| D547,154 | S | 7/2007 | Lee |
| 7,267,677 | B2 | 9/2007 | Johnson et al. |
| D564,662 | S | 3/2008 | Moses et al. |
| D567,943 | S | 4/2008 | Moses et al. |
| D575,395 | S | 8/2008 | Hushka |
| D575,401 | S | 8/2008 | Hixson et al. |
| D582,038 | S | 12/2008 | Swoyer et al. |
| D617,900 | S | 6/2010 | Kingsley et al. |
| D617,901 | S | 6/2010 | Unger et al. |
| D617,902 | S | 6/2010 | Twomey et al. |
| D617,903 | S | 6/2010 | Unger et al. |
| D618,798 | S | 6/2010 | Olson et al. |
| D621,503 | S | 8/2010 | Otten et al. |
| 7,799,028 | B2 | 9/2010 | Schechter et al. |
| D627,462 | S | 11/2010 | Kingsley |
| D628,289 | S | 11/2010 | Romero |
| D628,290 | S | 11/2010 | Romero |
| D630,324 | S | 1/2011 | Reschke |
| 7,861,906 | B2 | 1/2011 | Doll et al. |
| 7,918,230 | B2 | 4/2011 | Whitman et al. |
| D649,249 | S | 11/2011 | Guerra |
| D649,643 | S | 11/2011 | Allen, IV et al. |
| D661,394 | S | 6/2012 | Romero et al. |
| 8,333,765 | B2 | 12/2012 | Johnson et al. |
| 8,454,602 | B2 | 6/2013 | Kerr et al. |
| 8,523,898 | B2 | 9/2013 | Bucciaglia et al. |
| 8,529,566 | B2 | 9/2013 | Kappus et al. |
| 8,568,408 | B2 | 10/2013 | Townsend et al. |
| 8,579,176 | B2 | 11/2013 | Smith et al. |
| 8,591,510 | B2 | 11/2013 | Allen, IV et al. |
| 8,628,557 | B2 | 1/2014 | Collings et al. |
| 8,679,098 | B2 | 3/2014 | Hart |
| 8,679,140 | B2 | 3/2014 | Butcher |
| 8,685,009 | B2 | 4/2014 | Chernov et al. |
| 8,685,056 | B2 | 4/2014 | Evans et al. |
| 8,696,667 | B2 | 4/2014 | Guerra et al. |
| 8,702,737 | B2 | 4/2014 | Chojin et al. |
| 8,702,749 | B2 | 4/2014 | Twomey |
| 8,745,840 | B2 | 6/2014 | Hempstead et al. |
| 8,747,413 | B2 | 6/2014 | Dycus |
| 8,747,434 | B2 | 6/2014 | Larson et al. |
| 8,752,264 | B2 | 6/2014 | Ackley et al. |
| 8,756,785 | B2 | 6/2014 | Allen, IV et al. |
| 8,845,636 | B2 | 9/2014 | Allen, IV et al. |
| 8,852,185 | B2 | 10/2014 | Twomey |
| 8,864,753 | B2 | 10/2014 | Nau, Jr. et al. |
| 8,864,795 | B2 | 10/2014 | Kerr et al. |
| 8,887,373 | B2 | 11/2014 | Brandt et al. |
| 8,888,771 | B2 | 11/2014 | Twomey |
| 8,900,232 | B2 | 12/2014 | Ourada |
| 8,920,461 | B2 | 12/2014 | Unger et al. |
| 8,939,972 | B2 | 1/2015 | Twomey |
| 8,961,513 | B2 | 2/2015 | Allen, IV et al. |
| 8,961,514 | B2 | 2/2015 | Garrison |
| 8,961,515 | B2 | 2/2015 | Twomey et al. |
| 8,968,283 | B2 | 3/2015 | Kharin |
| 8,968,298 | B2 | 3/2015 | Twomey |
| 8,968,305 | B2 | 3/2015 | Dumbauld et al. |
| 8,968,306 | B2 | 3/2015 | Unger |
| 8,968,307 | B2 | 3/2015 | Evans et al. |

(56) References Cited

U.S. PATENT DOCUMENTS

| | | |
|---|---|---|
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,055,961 B2 | 6/2015 | Manzo et al. |
| 9,060,780 B2 | 6/2015 | Twomey et al. |
| 9,072,524 B2 | 7/2015 | Heard et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 9,192,432 B2 | 11/2015 | Larson et al. |
| 9,259,268 B2 | 2/2016 | Behnke, II et al. |
| 9,265,565 B2 | 2/2016 | Kerr |
| 9,265,568 B2 | 2/2016 | Chernov et al. |
| 9,265,569 B2 | 2/2016 | Hart et al. |
| 9,314,295 B2 | 4/2016 | Garrison |
| 9,375,258 B2 | 6/2016 | Kendrick |
| 9,375,263 B2 | 6/2016 | Allen, IV et al. |
| 9,375,282 B2 | 6/2016 | Nau, Jr. et al. |
| 9,381,059 B2 | 7/2016 | Garrison |
| 9,456,870 B2 | 10/2016 | Chernov et al. |
| 9,474,569 B2 | 10/2016 | Manzo et al. |
| 9,486,220 B2 | 11/2016 | Twomey et al. |
| 9,492,221 B2 | 11/2016 | Garrison |
| 9,615,877 B2 | 4/2017 | Tyrrell et al. |
| 9,636,169 B2 | 5/2017 | Allen, IV et al. |
| 9,668,806 B2 | 6/2017 | Unger et al. |
| 9,693,816 B2 | 7/2017 | Orszulak |
| 9,713,493 B2 | 7/2017 | Waaler et al. |
| 9,820,765 B2 | 11/2017 | Allen, IV et al. |
| 9,844,384 B2 | 12/2017 | Chernov et al. |
| 9,956,030 B2 | 5/2018 | Allen, IV et al. |
| 10,117,705 B2 | 11/2018 | Chernov et al. |
| 10,271,897 B2 | 4/2019 | Allen, IV et al. |
| 10,731,740 B1 | 8/2020 | Cui et al. |
| 2002/0058925 A1 | 5/2002 | Kaplan et al. |
| 2002/0062131 A1 | 5/2002 | Gallo |
| 2002/0099371 A1 | 7/2002 | Schulze et al. |
| 2002/0161364 A1 | 10/2002 | Mulier et al. |
| 2002/0177842 A1 | 11/2002 | Weiss |
| 2003/0060816 A1 | 3/2003 | Iida |
| 2003/0125734 A1 | 7/2003 | Mollenauer |
| 2003/0208186 A1 | 11/2003 | Moreyra |
| 2004/0148992 A1 | 8/2004 | Huang |
| 2004/0193153 A1 | 9/2004 | Sartor et al. |
| 2004/0254573 A1 | 12/2004 | Dycus et al. |
| 2005/0090837 A1 | 4/2005 | Sixto, Jr. |
| 2005/0240218 A1 | 10/2005 | Freed et al. |
| 2006/0022015 A1 | 2/2006 | Shelton et al. |
| 2006/0025811 A1 | 2/2006 | Shelton |
| 2006/0052777 A1 | 3/2006 | Dumbauld |
| 2006/0161138 A1 | 7/2006 | Orban et al. |
| 2007/0233052 A1 | 10/2007 | Brock |
| 2008/0015631 A1 | 1/2008 | Lee et al. |
| 2008/0083257 A1 | 4/2008 | Taylor et al. |
| 2008/0134812 A1 | 6/2008 | Murata |
| 2008/0264139 A1 | 10/2008 | Rosenbohm et al. |
| 2008/0319442 A1 | 12/2008 | Unger et al. |
| 2008/0319467 A1 | 12/2008 | Wenchell |
| 2009/0088743 A1 | 4/2009 | Masuda |
| 2009/0182327 A1 | 7/2009 | Unger |
| 2010/0094287 A1 | 4/2010 | Cunningham et al. |
| 2010/0145334 A1 | 6/2010 | Olson et al. |
| 2010/0274265 A1 | 10/2010 | Wingardner et al. |
| 2010/0292691 A1 | 11/2010 | Brogna |
| 2011/0009864 A1 | 1/2011 | Bucciaglia et al. |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2011/0144665 A1 | 6/2011 | Malkowski |
| 2011/0301600 A1 | 12/2011 | Garrison et al. |
| 2012/0022527 A1 | 1/2012 | Woodruff et al. |
| 2012/0024936 A1* | 2/2012 | Baxter, III ........ A61B 17/07207 227/180.1 |
| 2012/0239034 A1 | 9/2012 | Horner et al. |
| 2012/0259331 A1 | 10/2012 | Garrison |
| 2012/0265241 A1 | 10/2012 | Hart et al. |
| 2012/0296238 A1 | 11/2012 | Chernov et al. |
| 2012/0296371 A1 | 11/2012 | Kappus et al. |
| 2012/0303026 A1 | 11/2012 | Dycus et al. |
| 2012/0330308 A1 | 12/2012 | Joseph |
| 2013/0022495 A1 | 1/2013 | Allen, IV et al. |
| 2013/0071282 A1 | 3/2013 | Fry |
| 2013/0079774 A1 | 3/2013 | Whitney et al. |
| 2013/0123783 A1 | 5/2013 | Marczyk et al. |
| 2013/0274736 A1 | 10/2013 | Garrison |
| 2013/0304066 A1 | 11/2013 | Kerr et al. |
| 2014/0276723 A1 | 9/2014 | Parihar et al. |
| 2017/0042560 A1 | 2/2017 | Lee et al. |
| 2017/0150975 A1 | 6/2017 | Bozung |
| 2017/0265951 A1 | 9/2017 | Grover et al. |
| 2017/0273749 A1 | 9/2017 | Grover et al. |
| 2017/0365923 A1 | 12/2017 | Schmutzler et al. |
| 2018/0028271 A1 | 2/2018 | Rockrohr |
| 2018/0071037 A1 | 3/2018 | Grover et al. |
| 2019/0008600 A1 | 1/2019 | Pedros et al. |
| 2019/0015124 A1* | 1/2019 | Williams ............. A61B 17/282 |
| 2019/0099227 A1 | 4/2019 | Rockrohr |
| 2019/0274769 A1 | 9/2019 | Perdue et al. |
| 2020/0237453 A1 | 7/2020 | Anglese |
| 2020/0237455 A1 | 7/2020 | Anglese |
| 2020/0246058 A1 | 8/2020 | Traina |
| 2020/0253676 A1 | 8/2020 | Traina |
| 2020/0261166 A1 | 8/2020 | Anglese |
| 2020/0261167 A1 | 8/2020 | Anglese |
| 2020/0261168 A1 | 8/2020 | Anglese |
| 2020/0305956 A1* | 10/2020 | Behymer ........... A61B 17/2909 |

\* cited by examiner

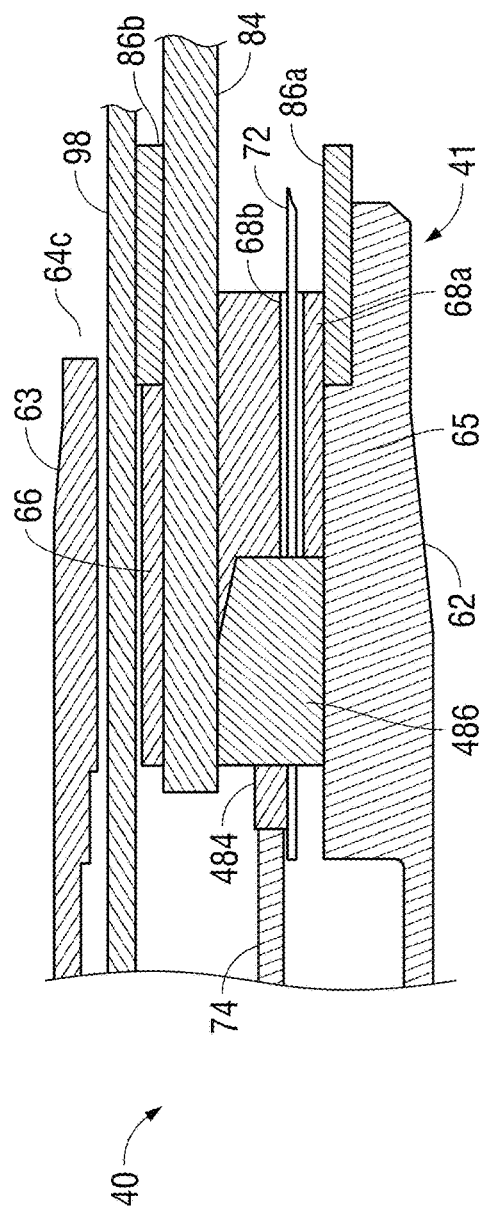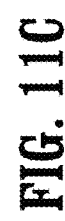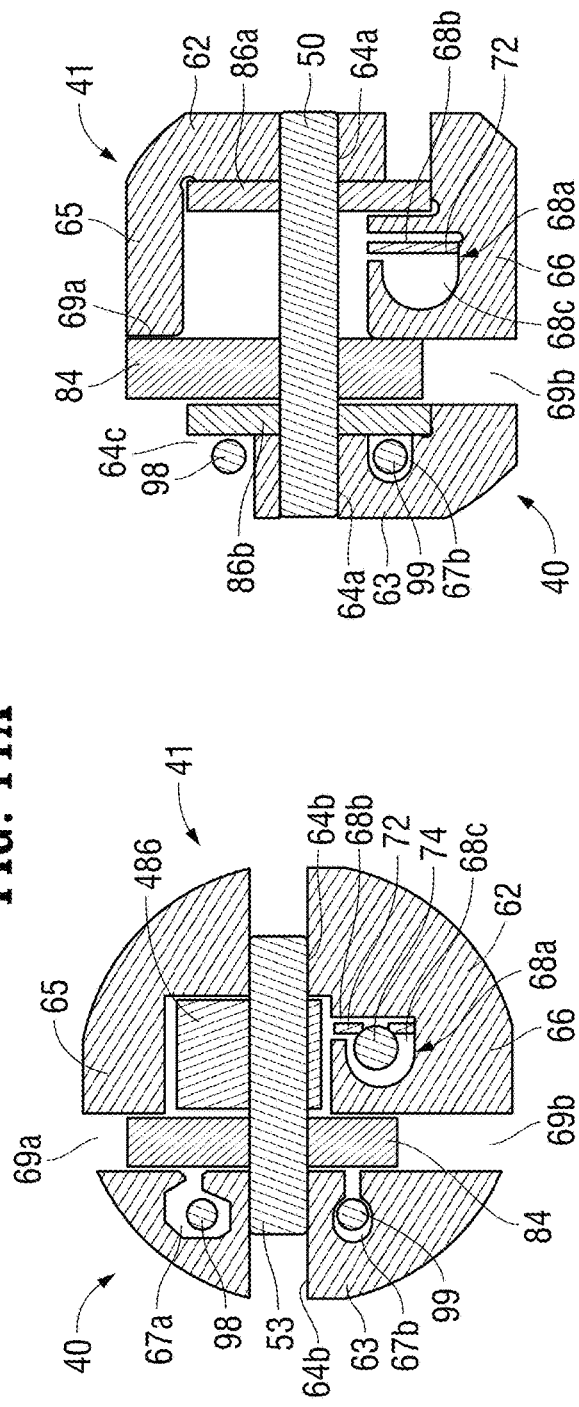

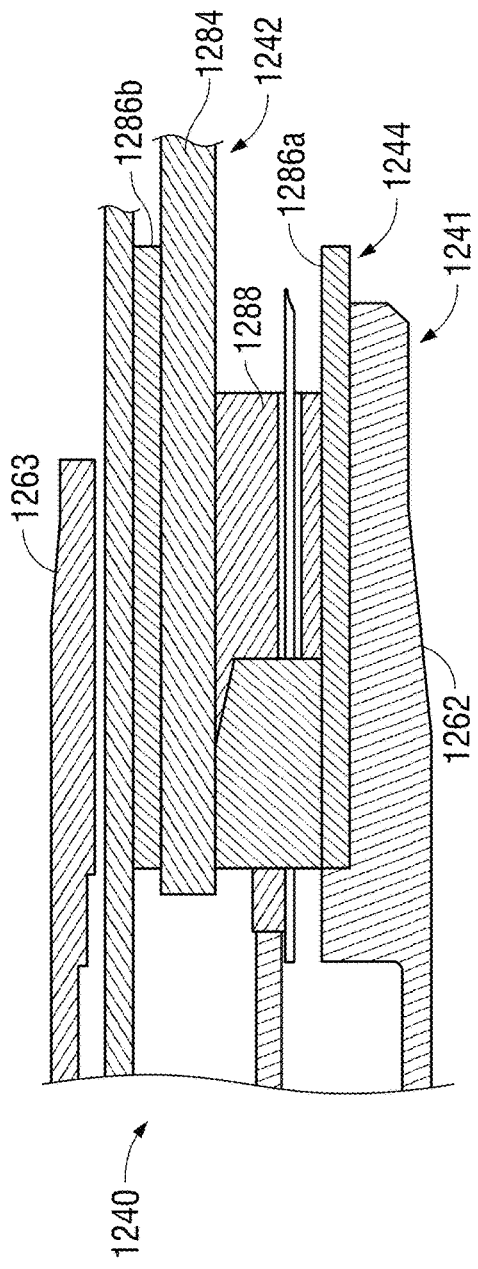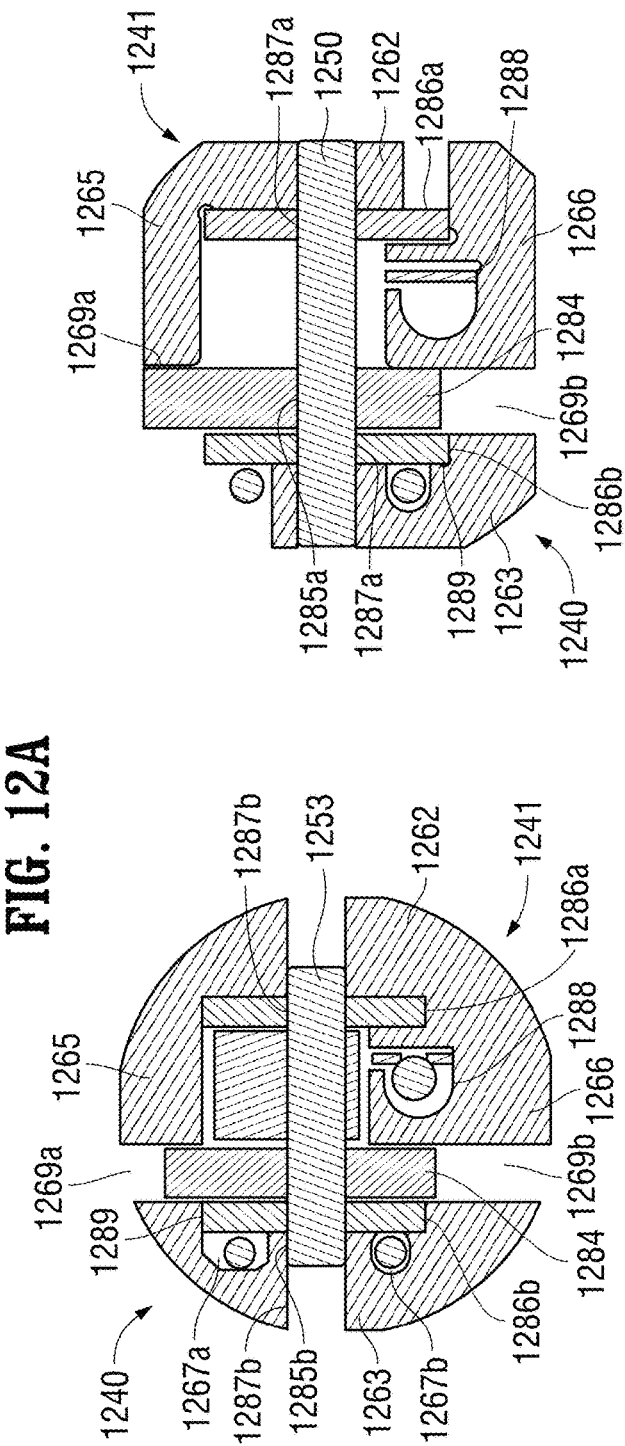
FIG. 12A
FIG. 12B
FIG. 12C

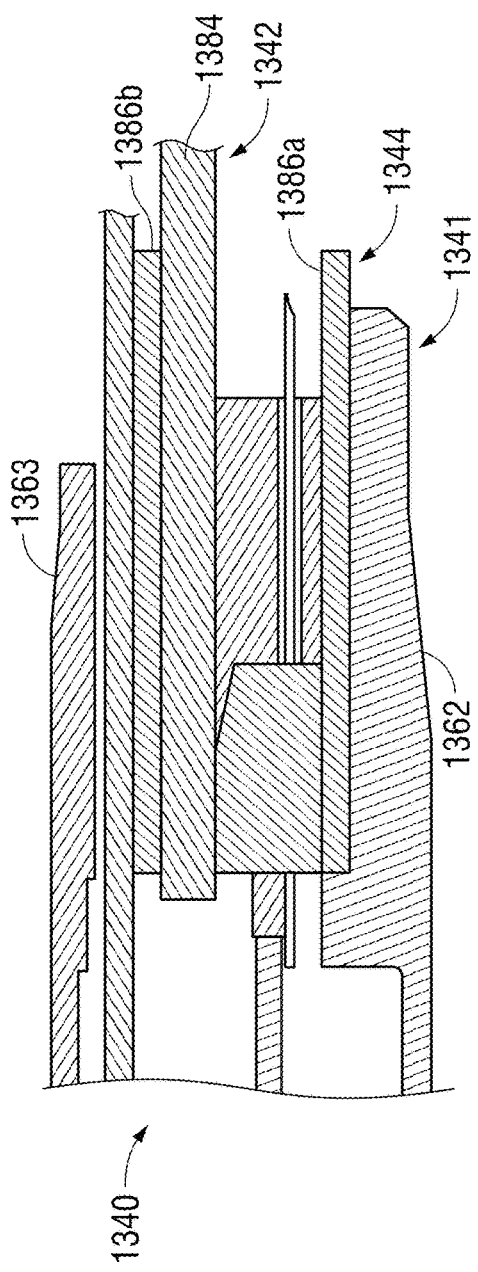
FIG. 13A
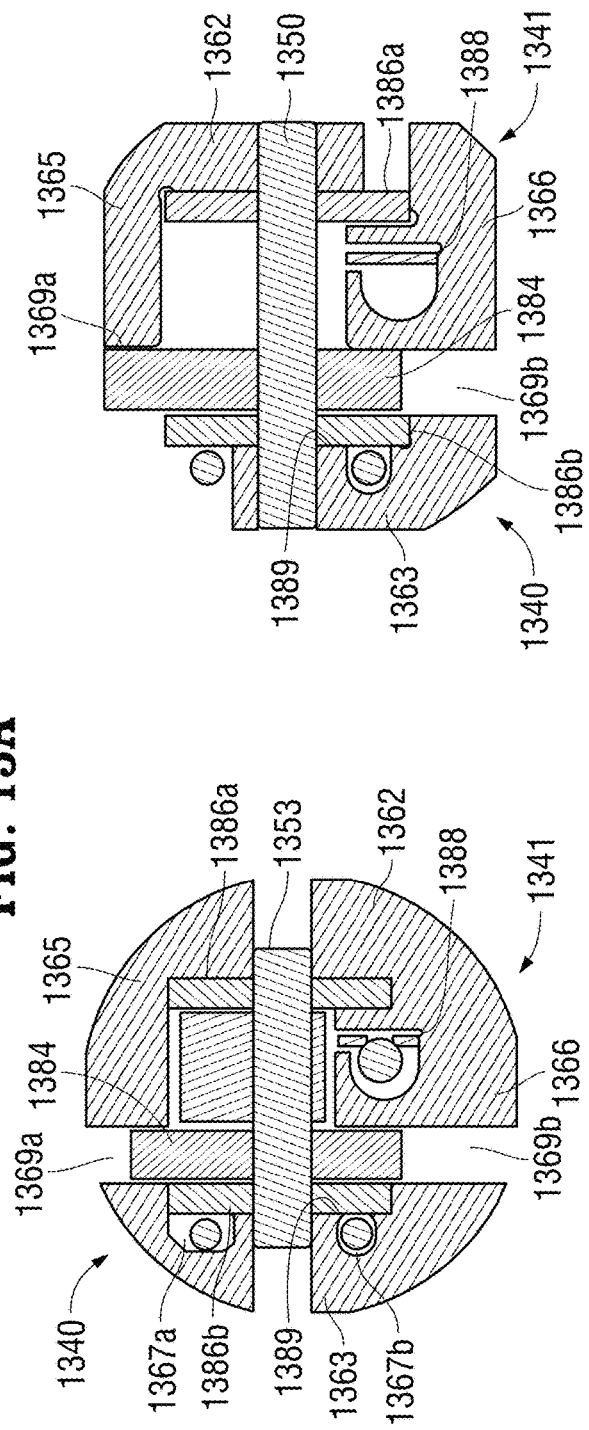
FIG. 13B
FIG. 13C

END EFFECTOR ASSEMBLIES FOR SURGICAL INSTRUMENTS SUCH AS FOR USE IN ROBOTIC SURGICAL SYSTEMS

FIELD

The present disclosure relates to surgical instruments and, more specifically, to end effector assemblies for surgical instruments such as for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

A surgical forceps, one type of instrument capable of being utilized with a robotic surgical system, relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the tissue is severed using a cutting element. Accordingly, electrosurgical forceps are designed to incorporate a cutting element to effectively sever treated tissue. Alternatively, energy-based, e.g., thermal, electrical, ultrasonic, etc., cutting mechanisms may be implemented.

SUMMARY

As used herein, the term "distal" refers to the portion that is being described which is further from an operator (whether a human surgeon or a surgical robot), while the term "proximal" refers to the portion that is being described which is closer to the operator. The terms "about," substantially," and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is an end effector assembly of a surgical instrument. The end effector assembly includes a clevis, a pivot pin, a cam pin, and first and second jaw members. The clevis includes a proximal body, first and second arms extending distally from the proximal body in spaced-apart relation relative to one another arms, a ceiling extending at least partially between upper portions of the first and second arms, and a floor extending at least partially between lower portion of the first and second arms. The pivot pin extends transversely at least partially between the first and second arms of the clevis. The cam pin extends transversely at least partially between the first and second arms of the clevis and is positioned proximally of the pivot pin. The first jaw member includes a proximal extension portion disposed at least partially within the clevis and a distal jaw body extending distally from the clevis. The proximal extension portion of the first jaw member includes a first flag disposed between the first and second arms of the clevis and extending vertically at least partially through openings defined within the ceiling and floor to inhibit lateral motion thereof.

The first flag further defines a pivot aperture through which the pivot pin extends and a cam slot through which the cam pin extends. The second jaw member includes a proximal extension portion disposed at least partially within the clevis and a distal jaw body extending distally from the clevis. The proximal extension portion of the second jaw member includes second and third flags disposed between the first and second arms of the clevis in spaced-apart relative to one another and between the ceiling and the floor. The second and third flags and fixedly engaged to the clevis, define pivot apertures through which the pivot pin extends, and terminate distally of the cam pin. The first flag is disposed between the second and third flags in an offset position such that the first flag is disposed closer to the third flag than the second flag.

In an aspect of the present disclosure, the third flag is captured between the second arm of the clevis and the first flag.

In another aspect of the present disclosure, the clevis further includes a cutter guide disposed between the first and second arms. In such aspects, the cutter guide may define a first portion configured to slidably receive a cutting element, and a second portion configured to slidably receive a drive structure associated with the cutting element. Additionally or alternatively, the second flag may be captured between the first arm of the clevis and the cutter guide.

In another aspect of the present disclosure, the clevis is configured to receive a cam block supporting the cam pin thereon. The cam block is slidably disposed within the clevis between the first flag and the second flag.

In still another aspect of the present disclosure, sliding of the cam block through the clevis slides the cam pin through the cam slot to pivot the distal jaw body of the first jaw member relative to the distal jaw body of the second jaw member between a spaced-apart position and an approximated position.

In yet another aspect of the present disclosure, the cam block, in a distal-most position, partially surrounds the pivot pin.

In still yet another aspect of the present disclosure, the second arm of the clevis defines first and second wire channels extending therethrough outwardly of the third flag In another aspect of the present disclosure, the first flag defines a height greater than heights of each of the second and third flags.

Another end effector assembly of a surgical instrument provided in accordance with aspects of the present disclosure includes a clevis including a proximal body, a pivot pin, a cam pin, and first and second jaw members. The clevis includes first and second arms extending distally from the proximal body in spaced-apart relation relative to one another arms, a ceiling extending at least partially between upper portions of the first and second arms, and a floor extending at least partially between lower portion of the first and second arms. The pivot pin and the cam pin extend transversely at least partially between the first and second arms of the clevis. The first jaw member includes a proximal extension portion disposed at least partially within the clevis and a distal jaw body extending distally from the clevis. The proximal extension portion of the first jaw member includes a first flag disposed between the first and second arms of the clevis and extending vertically at least partially through openings defined within the ceiling and floor. The first flag defines a pivot aperture through which the pivot pin extends and a cam slot through which the cam pin extends. The second jaw member includes a proximal extension portion disposed at least partially within the clevis and a distal jaw body extending distally from the clevis. The proximal extension portion of the second jaw member includes second and third flags disposed between the first and second arms of the clevis in spaced-apart relative to one another and between the ceiling and the floor. The second and third flags and fixedly engaged to the clevis, define pivot apertures through which the pivot pin extends, and define cam slots through which the cam pin extends. The third flag is at least partially disposed within a recess defined within the second arm of the clevis. The first flag is disposed between the second and third flags in an offset position such that the first flag is disposed closer to the third flag than the second flag.

In an aspect of the present disclosure, the third flag is fully disposed within the recess and the first flag extends vertically at least partially through the openings defined within the ceiling and floor such that the ceiling and floor inhibit lateral motion of the first flag.

In another aspect of the present disclosure, the third flag is partially disposed within the recess and a portion thereof protrudes inwardly therefrom. The first flag, in such aspects, extends vertically at least partially through the openings defined within the ceiling and floor and the protruding portion of the third flag together with the ceiling and floor inhibit lateral motion of the first flag.

In still another aspect of the present disclosure, the clevis further includes a cutter guide disposed between the first and second arms. In such aspects, the cutter guide may define a first portion configured to slidably receive a cutting element, and a second portion configured to slidably receive a drive structure associated with the cutting element. Additionally or alternatively, the second flag may be captured between the first arm of the clevis and the cutter guide.

In yet another aspect of the present disclosure, the clevis is configured to receive a cam block supporting the cam pin thereon. The cam block is slidably disposed within the clevis between the first flag and the second flag.

In still yet another aspect of the present disclosure, sliding of the cam block through the clevis slides the cam pin through the cam slots to pivot the distal jaw body of the first jaw member relative to the distal jaw body of the second jaw member between a spaced-apart position and an approximated position.

In another aspect of the present disclosure, the second arm of the clevis defines first and second wire channels extending therethrough outwardly of the third flag.

In another aspect of the present disclosure, the first flag defines a height greater than heights of each of the second and third flags.

BRIEF DESCRIPTION OF THE DRAWINGS

Various aspects and features of the present disclosure are described hereinbelow with reference to the drawings wherein:

FIGS. 11A-11C are longitudinal cross-sectional, first distally-facing transverse cross-sectional, and second distally-facing transverse cross-sectional views of the end effector assembly as illustrated in FIG. 4;

FIGS. 12A-12C are longitudinal cross-sectional, first distally-facing transverse cross-sectional, and second distally-facing transverse cross-sectional views of another end effector assembly configured for use with the surgical instrument of FIG. 1; and FIGS. 13A-13C are longitudinal cross-sectional, first distally-facing transverse cross-sectional, and second distally-facing transverse cross-sectional views of yet another end effector assembly configured for use with the surgical instrument of FIG. 1.

DETAILED DESCRIPTION

Figure 1:
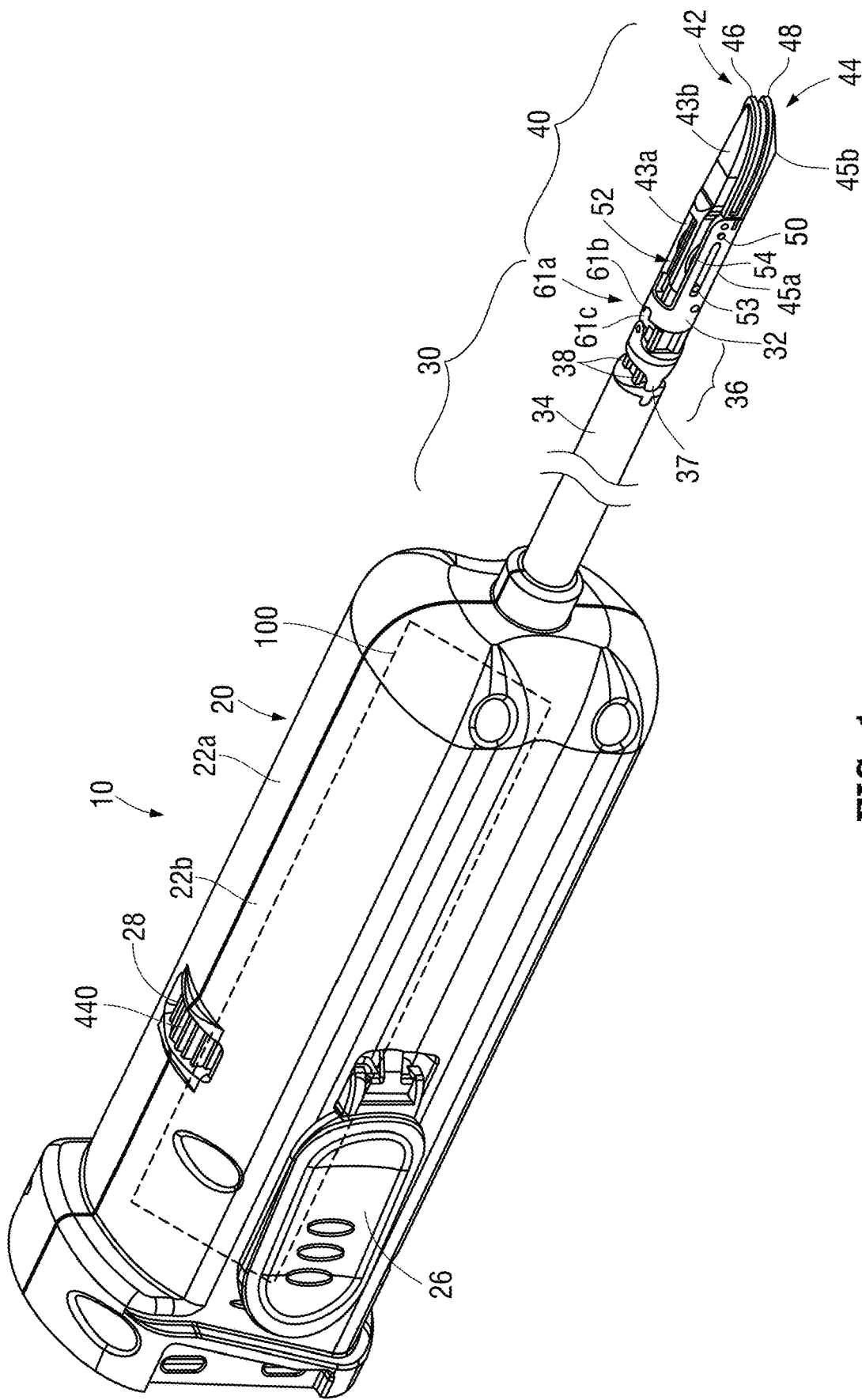
FIG. 1 is a perspective view of a surgical instrument in accordance with the present disclosure configured for mounting on a robotic arm of a robotic surgical system.
Figure 2:
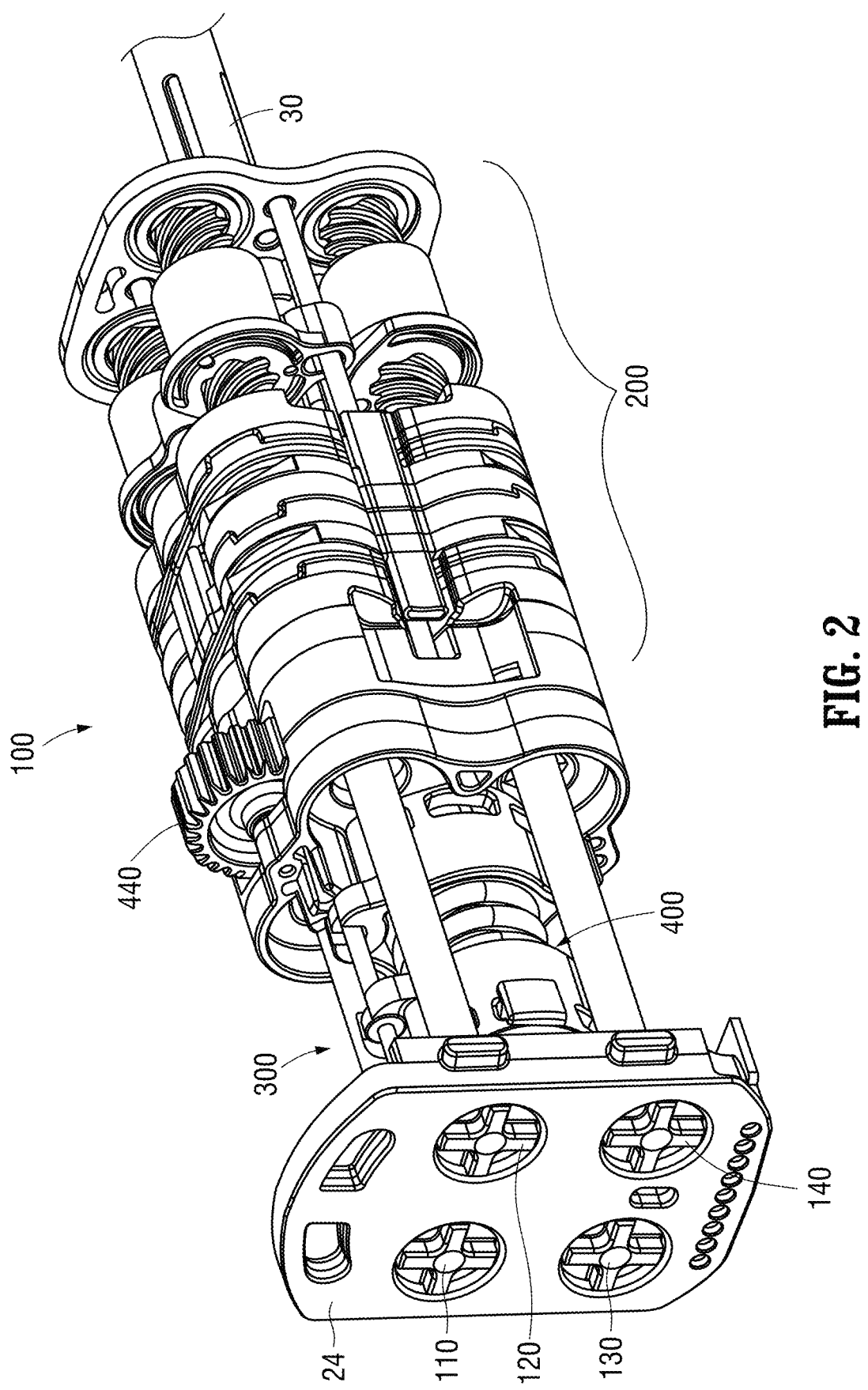
FIG. 2 is a rear perspective view of a proximal portion of the surgical instrument of FIG. 1 with an outer housing removed.
Figure 3:
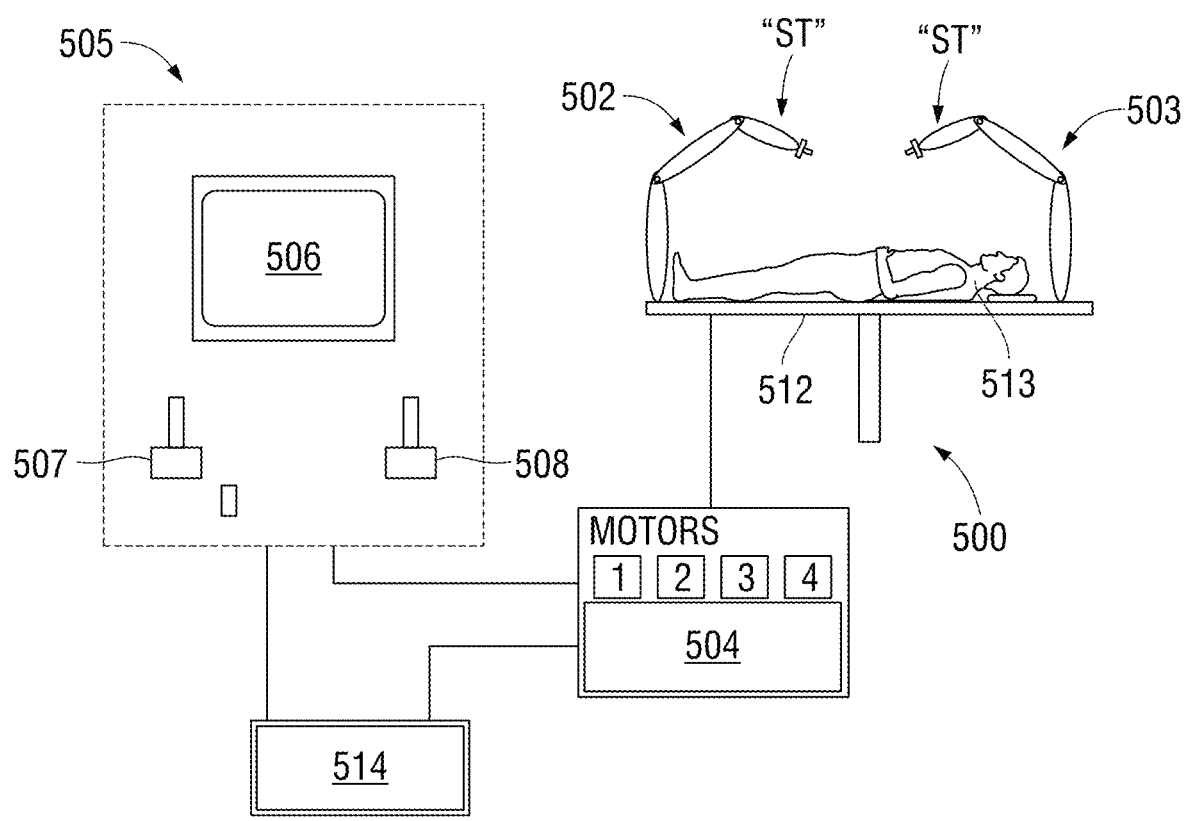
FIG. 3 is a schematic illustration of an exemplary robotic surgical system configured to releasably receive the surgical instrument of FIG. 1.

Referring to FIGS. 1 and 2, a surgical instrument 10 provided in accordance with the present disclosure generally includes a housing 20, a shaft 30 extending distally from housing 20, an end effector assembly 40 extending distally from shaft 30, and an actuation assembly 100 disposed within housing 20 and operably associated with shaft 30 and end effector assembly 40. Instrument 10 is detailed herein as an articulating electrosurgical forceps configured for use with a robotic surgical system, e.g., robotic surgical system 500 (FIG. 3). However, the aspects and features of instrument 10 provided in accordance with the present disclosure, detailed below, are equally applicable for use with other suitable surgical instruments (including non-robotic surgical instrument) and/or in other suitable surgical systems (including non-robotic surgical systems).

Housing 20 of instrument 10 includes first and second body portion 22a, 22b and a proximal face plate 24 (FIG. 2) that cooperate to enclose actuation assembly 100 therein. Proximal face plate 24 includes apertures defined therein through which inputs 110-140 of actuation assembly 100 extend. A pair of latch levers 26 (only one of which is illustrated in FIG. 1) extends outwardly from opposing sides of housing 20 and enables releasable engagement (directly or indirectly) of housing 20 with a robotic arm of a surgical system, e.g., robotic surgical system 500 (FIG. 3). An aperture 28 defined through housing 20 permits thumbwheel 440 to extend therethrough to enable manual manipulation of thumbwheel 440 from the exterior of housing 20 to permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extends through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation assembly 200 of actuation assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, actuation of articulation cables 38 is effected in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

Figure 7:
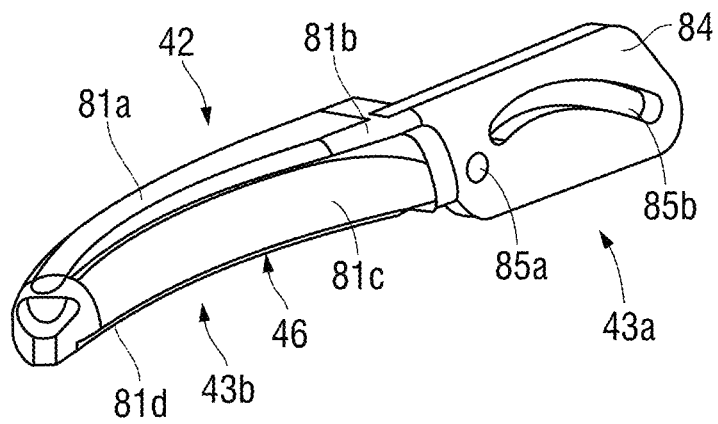
FIG. 7 is a perspective view of a movable jaw member of the end effector assembly as illustrated in FIG. 4.
Figure 8:
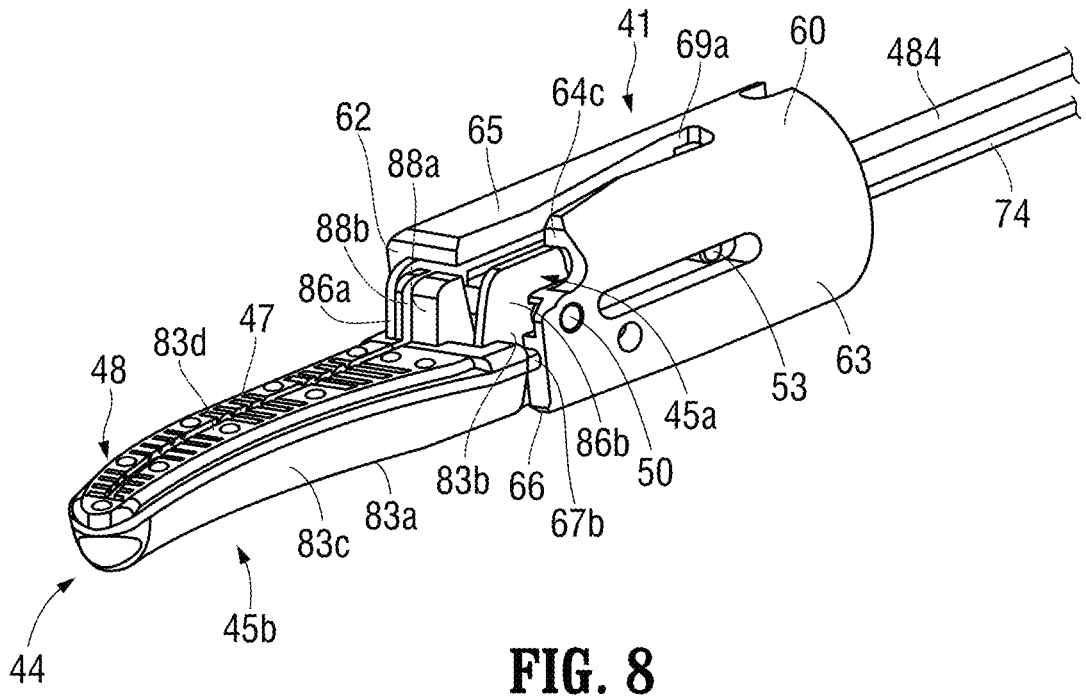
FIG. 8 is a perspective view of the end effector assembly as illustrated in FIG. 4 with the movable jaw member removed.
Figure 9:
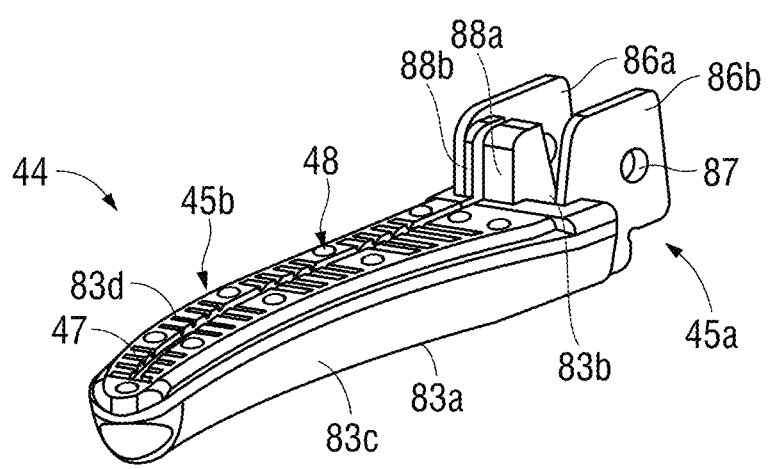
FIG. 9 is a perspective view of the fixed jaw member of the end effector assembly as illustrated in FIG. 4.

End effector assembly 40 includes a clevis 41 (extending from, integrally formed with, or constituting distal segment 32 of shaft 30) supporting first and second jaw members 42, 44, respectively. Each jaw member 42, 44 includes a proximal extension portion 43a, 45a and a distal body portion 43b, 45b, respectively. Distal body portions 43b, 45b define opposed tissue-contacting surfaces 46, 48, respectively. Proximal extension portions 43a, 45a are pivotably coupled to one another about a pivot pin 50 and are operably coupled to one another via a cam-slot assembly 52 including a cam pin 53 slidably received within cam slots 64b defined within the proximal extension portion 43a of jaw member 42 (FIG. 7), to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

Figure 4:
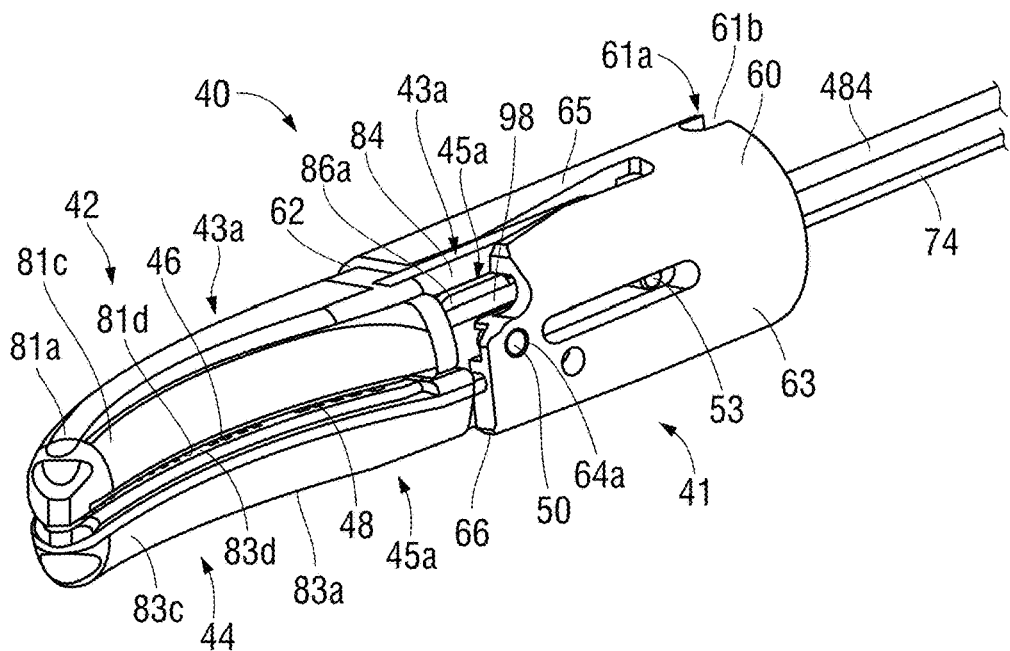
FIG. 4 is an enlarged, perspective view of an end effector assembly of the surgical instrument of FIG. 1.
Figure 5:
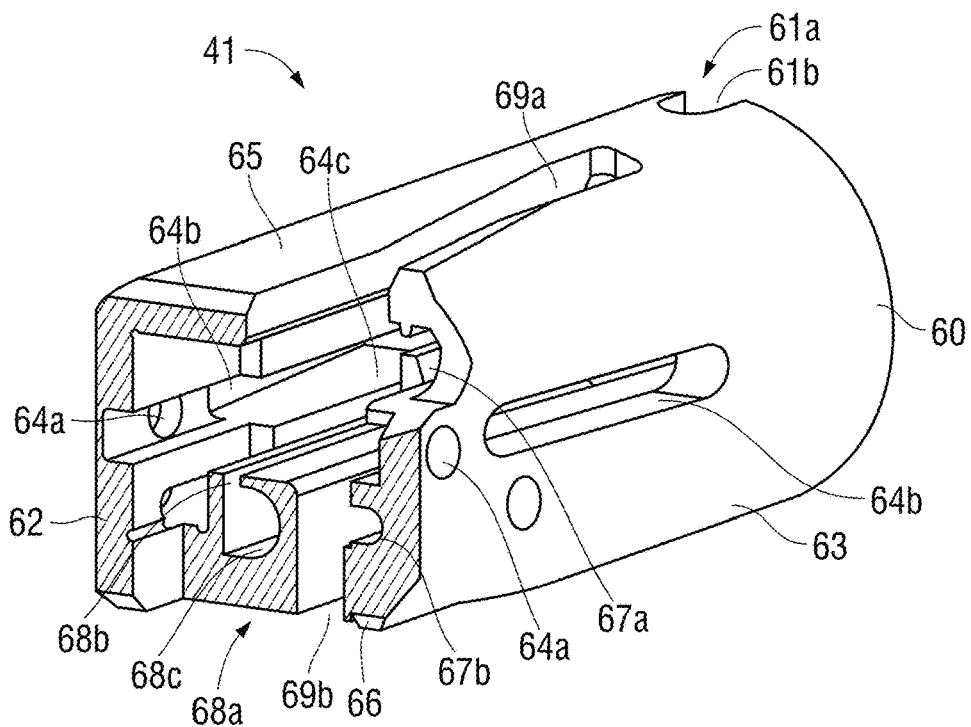
FIG. 5 is a perspective view of a clevis of the end effector assembly as illustrated in FIG. 4.
Figure 6:
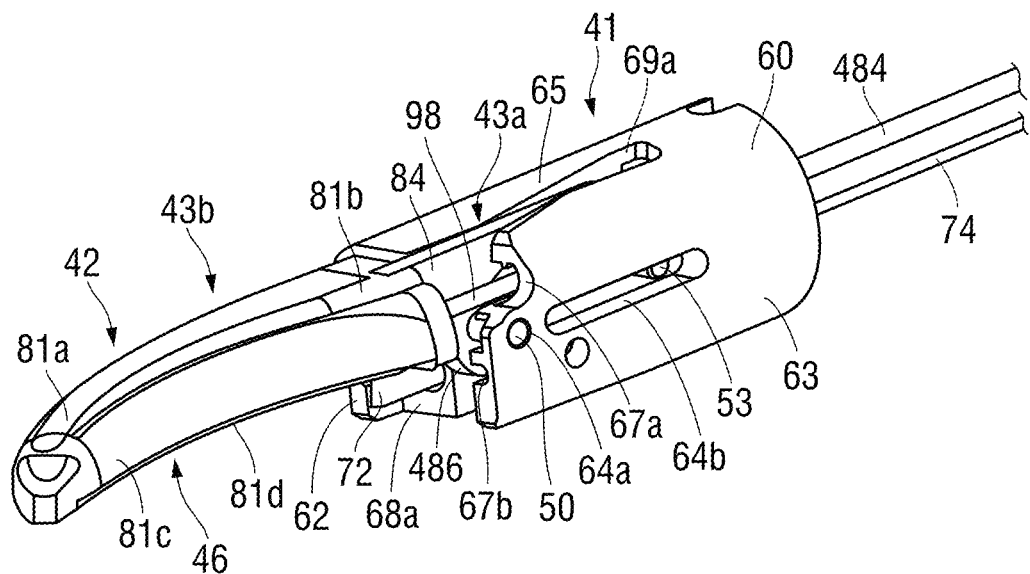
FIG. 6 is a perspective view of the end effector assembly as illustrated in FIG. 4 with a fixed jaw member removed.

Longitudinally-extending channels, e.g., channel 47 of jaw member 44 (FIGS. 4 and 5) and/or a corresponding channel (not shown) of jaw member 42, are defined through tissue-contacting surfaces 46, 48, respectively, of jaw members 42, 44. A cutting assembly 70 (FIG. 10) is provided including a selectively advanceable cutting element 72, e.g., a knife, that enables cutting of tissue grasped between tissue-contacting surfaces 46, 48 of jaw members 42, 44, respectively. A cutting drive assembly 300 (FIG. 2) of actuation assembly 100 provides for selective actuation of cutting assembly 70 to reciprocate the cutting element 72 through jaw members 42, 44 to cut tissue grasped between tissue-contacting surfaces 46, 48. Cutting drive assembly 300 (FIG. 2) is operably coupled between a cutting actuation rod 74 of cutting assembly 70 (FIG. 10) and third input 130 of actuation assembly 100 such that, upon receipt of appropriate rotational input into third input 130, cutting drive assembly 300 manipulates cutting actuation rod 74 to reciprocate cutting element 72 between jaw members 42, 44 to cut tissue grasped between tissue-contacting surfaces 46, 48.

Continuing with reference to FIGS. 1 and 2, a drive rod 484 (FIG. 10) is operably coupled to cam-slot assembly 52 of end effector assembly 40, e.g., engaged with cam pin 53 thereof, such that longitudinal actuation of drive rod 484 (FIG. 10) pivots jaw member 42 relative to jaw member 44 between the spaced-apart and approximated positions. More specifically, urging drive rod 484 (FIG. 10) proximally pivots jaw member 42 relative to jaw member 44 towards the approximated position while urging drive rod 484 (FIG. 10) distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 (FIG. 10) (or other suitable structure(s)) are also contemplated. Drive rod 484 (FIG. 10) extends proximally from end effector assembly 40 through shaft 30 and into housing 20 wherein drive rod 484 (FIG. 10) is operably coupled with a jaw drive assembly 400 of actuation assembly 100 (FIG. 2) to enable selective actuation of end effector assembly 40 to grasp tissue therebetween and apply a closure force within an appropriate jaw closure force range.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, etc., through tissue grasped therebetween for energy-based tissue treatment. Instrument 10 defines conductive pathways extending through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator via an electrosurgical cable extending therebetween, for supplying energy to tissue-contacting surfaces 46, 48 to treat, e.g., seal, tissue grasped between tissue-contacting surfaces 46, 48. The electrically conductive pathways to tissue-contacting surfaces 46, 48 of jaw members 42, 44, are illustrated, for example, as respective first and second lead wires 98, 99 (see FIG. 10).

As noted above, actuation assembly 100 is disposed within housing 20 and includes an articulation assembly 200, cutting drive assembly 300, and jaw drive assembly 400. Articulation assembly 200 is operably coupled between first and second inputs 110, 120, respectively, of actuation assembly 100 and articulation cables 38 (FIG. 1) such that, upon receipt of appropriate rotational inputs into first and/or second inputs 110, 120, articulation assembly 200 manipulates cables 38 (FIG. 1) to articulate end effector assembly 40 in a desired direction, e.g., to pitch and/or yaw end effector assembly 40. Cutting drive assembly 300, s noted above, enables reciprocation of cutting element 72 (FIG. 10) between jaw members 42, 44 to cut tissue grasped between tissue-contacting surfaces 46, 48 in response to receipt of appropriate rotational input into third input 130. Jaw drive assembly 400 is operably coupled between fourth input 140 of actuation assembly 100 and drive rod 484 (FIG. 10) such that, upon receipt of appropriate rotational input into fourth input 140, jaw drive assembly 400 pivots jaw members 42, 44 between the spaced-apart and approximated positions to grasp tissue therebetween and apply a closure force within an appropriate closure force range.

Actuation assembly 100 is configured to operably interface with a robotic surgical system 500 (FIG. 3) when instrument 10 is mounted on robotic surgical system 500 (FIG. 3), to enable robotic operation of actuation assembly 100 to provide the above-detailed functionality. That is, robotic surgical system 500 (FIG. 3) selectively provides rotational inputs to inputs 110-140 of actuation assembly 100 to articulate end effector assembly 40, grasp tissue between jaw members 42, 44, and/or cut tissue grasped between jaw members 42, 44. However, it is also contemplated that actuation assembly 100 be configured to interface with any other suitable surgical system, e.g., a manual surgical handle, a powered surgical handle, etc. For the purposes herein, robotic surgical system 500 (FIG. 3) is generally described.

Turning to FIG. 3, robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, pre-operative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be instrument 10 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

Turning to FIGS. 4-10, end effector assembly 40 is shown and described in greater detail. More specifically, as noted above, end effector assembly 40 includes clevis 41 and first and second jaw members 42, 44, respectively, supported by clevis 41. Drive rod 484, first and second lead wires 98, 99, cutting element 72, and cutting actuation rod 74 extend at least partially through end effector assembly 40 to enable the manipulation of jaw member 42 relative to jaw member 44 to grasp tissue therebetween, the supply of electrosurgical (or other suitable) energy to tissue-contacting surfaces 46, 48 for treating, e.g., sealing, tissue grasped therebetween, and/or the advancement of cutting element 72 to cut grasped (and, in some configurations, treated) tissue.

With reference in particular to FIGS. 5 and 11A-11C, in conjunction with FIGS. 4, 6, 8, and 10, clevis 41 may be monolithically formed as a single piece of material or, alternatively, via two or more pieces of material formed separately and subsequently joined to one another. Clevis 41 includes or defines various features, e.g., supports, slots, channels, passages, apertures, openings, etc., as detailed below, that operably support, retain, and/or guide jaw members 42, 44, drive rod 484, cutting element 72, cutting actuation rod 74, and first and second lead wires 98, 99. In this manner, clevis 41: pivotably supports jaw member 42 relative to jaw member 44; fixedly supports jaw member 44; provides lateral support to jaw members 42, 44, e.g., inhibiting splay; guides translation of drive rod 484 to actuate jaw member 42; guide translation of cam pin 53 in response to translation of drive rod 484; guides advancement and retraction of cutting element 72 and cutting actuation rod 74; and routes, free from interfering or interference, first and second lead wires 98, 99 from shaft 30 (FIG. 1) to jaw members 42, 44.

Clevis 41, more specifically, includes a proximal body 60, a pair of spaced-apart arms 62, 63 extending distally from proximal body 60, a ceiling 65 extending across at least a portion of an upper open area defined by arms 62, 63, and a floor 66 extending across at least a portion of a lower open area defined by arms 62, 63. Proximal body 60 defines a keyed interface 61b configured to mate with a corresponding keyed interface 61c of a portion of distal segment 32 of shaft 30 or a distal-most articulating component 37 in fixed orientation relative thereto to establish a keyed engagement 61a therebetween (see FIG. 1). Proximal body 60 may further be secured thereto via, e.g., welding, snap-fit engagement, or in any other suitable manner. Arms 62, 63 define aligned apertures 64a extending transversely therethrough that are configured to receive the opposed ends of pivot pin 50 to retain pivot pin 50, and define aligned cam slots 64b extending transversely therethrough that are configured to receive the oppose ends of cam pin 53 to guide translation of cam pin 53. One of the arms, e.g., arm 63 further includes first and second wire channels 67a, 67b, respectively, configured to at least partially receive and guide first and second lead wires 98, 99 from shaft 30 (FIG. 1) to jaw members 42, 44. One of the arms, e.g., arm 62 also includes a cutting guide 68a protruding inwardly therefrom that defines a cutter channel 68b and a partially-cylindrical cut-out 68c that communicates with cutter channel 68b. Cutter channel 68b is configured to receive at least a portion of cutting element 72 while cut-out 68c is configured to receive at least a portion of cutting actuation rod 74 to guide translation of cutting element 72 and cutting actuation rod 74 into and through channel(s) 47 of jaw member 44 and/or jaw member 42.

Clevis 41 is further configured to receive, between arms 62, 63, cam block 486, which is engaged about a distal end portion of drive rod 484 and supports cam pin 53 thereon, to guide translation of cam block 486 and cam pin 53 in response to actuation of drive rod 484. Additionally, clevis 41 is configured to receive proximal extension portion 43a, 45a of jaw members 42, 44 between arms 62, 63, ceiling 65, and/or floor 66, as detailed below.

Referring to FIGS. 4 and 6-9, each jaw member 42, 44, as noted above, includes a proximal extension portion 43a, 45a and a distal body portion 43b, 45b. Jaw members 42, 44, more specifically, include structural jaws 81a, 83a, internal spacers 81b, 83b, outer housings 81c, 83c, and electrically-conductive plates 81d, 83d defining respective tissue-contacting surfaces 46, 48. Structural jaws 81a, 83a provides structural support to jaw members 42, 44 and include distal portions that support the components of distal body portions 43b, 45b of jaw members 42, 44, respectively, thereon, and proximal portions that extend proximally from distal body portions 43b, 45b to form proximal extension portion 43a, 45a of jaw members 42, 44. The proximal extension portion 43a, 45a of one of the jaw members, e.g., jaw member 44, may include a pair of spaced-apart flags 86a, 86b, while the proximal extension portion 43a, 45a of the other jaw member, e.g., jaw member 42, includes a single, offset flag 84. Other configurations, e.g., the reverse configuration or configurations wherein both of proximal extension portions 43a, 45a include one or two flags, are also contemplated. Flag 84 of proximal extension portion 43a of jaw member 42 defines a pivot aperture 85a and a cam slot 85b, which may be curved, angled, combinations thereof, or otherwise configured. Flags 86a, 86b of proximal extension portion 45a of jaw member 44 each define pivot apertures 87.

The distal portions of structural jaws 81a, 83a, together with internal spacers 81b, 83b, outer housings 81c, 83c, and electrically-conductive plates 81d, 83d, form distal body portions 43b, 45b of jaw members 42, 44. Internal spacers 81b, 83b are disposed on the distal portions of structural jaws 81a, 83a, respectively; electrically-conductive plates 81d, 83d are disposed on internal spacers 81sb, 83b, respectively; and outer housings 81c, 83c are disposed about internal spacers 81b, 83b, the distal portions of structural jaws 81a, 83a, and, in some configurations, a portion of the respective electrically-conductive plate 81d, 83d, to secure these components to one another, e.g., via overmolding, although other configurations are also contemplated.

As noted above, longitudinally-extending channel 47 of jaw member 44 and/or a corresponding channel (not shown) of jaw member 42 are defined through tissue-contacting surfaces 46, 48, respectively, of jaw members 42, 44. Channel 47 is formed by cooperating channel portions defined within electrically-conductive plate 83d and internal spacer 83b of jaw member 44. Internal spacer 83b further includes a partially-cylindrical cut-out (not explicitly shown; similar to and communicating with cut-out 68c of cutting guide 68a of clevis 41) that communicates with channel 47. Channel 47 and the cut-out are open at the proximal end of distal body portion 45b of jaw member 44 and communicate with cutter channel 68b and cut-out 68c (FIG. 5), respectively, to permit insertion of cutting element 72 and cutting actuation rod 74 (FIG. 6) therethrough. Jaw member 44 may additionally or alternatively include a tissue stop and cutting element guide 88a formed with and protruding upwardly from internal spacer 83b beyond tissue-contacting surface 48. Tissue stop and cutting element guide 88a defines a slot 88b for slidably receiving and guiding translation of cutting element 72 and also serves to inhibit tissue or debris from passing proximally into clevis 41.

Figure 10:
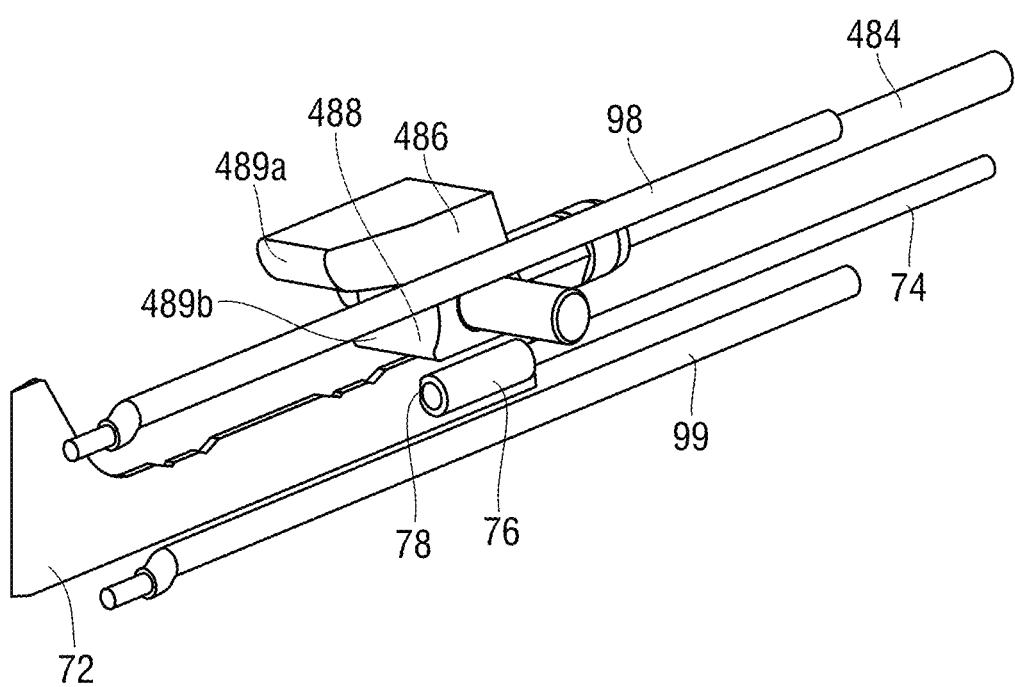
FIG. 10 is a perspective view illustrating distal portions of the electrical wires, jaw drive assembly, and knife drive assembly of the surgical instrument of FIG. 1.

Referring to FIG. 10, cutting assembly 70, as noted above, includes cutting element 72 and cutting actuation rod 74. A ferrule 76 engaged about a distal end portion of cutting actuation rod 74 is secured within a slot 78 defined within a proximal portion of cutting element 72 to securely engage cutting actuation rod 74 with cutting element 72 such that actuation of cutting actuation rod 74 reciprocates cutting element 72. Ferrule 76 and, thus, cutting actuation rod 74 are offset relative to cutting element 72 such that ferrule 76 and cutting actuation rod 74 protrude farther (or completely) from one side of cutting element 72 and less (or not at all) from the other side. Cutting element 72 and actuation rod 74 are configured for reciprocation through channel 47 and the cut-out, respectively, of jaw member 44 and/or a corresponding channel of jaw member 42 to cut tissue grasped between jaw members 42, 44 (see FIGS. 1, 4, 5, and 8).

Cam block 486 is engaged about a distal end portion of drive rod 484. Cam block 486 includes cam pin 53 protruding from either lateral side thereof such that one of the opposed ends of cam pin 53 may extend through cam slot 85b of flag 84 of proximal extension portion 41a of jaw member 42 and such that both opposed ends of cam pin 53 may extend at least partially into cam slots 64a defined within arms 62, 63 of clevis 41. Cam block 486 defines a contoured distally-facing surface 488 such that a forehead 489a thereof protrudes further distally than a body portion 489b thereof. In this manner, forehead 489a may extend distally in at least partially overlapping relation around pivot pin 50 while body portion 489b remains proximally of pivot pin 50. Forehead 489a may further include features and/or be received within features defined within clevis 41 to guide longitudinal translation thereof in response to actuation of drive rod 484.

Turning to FIGS. 11A-11C, ceiling 65 and floor 66 of clevis 41 define aligned openings 69a, 69b, respectively, that receive upper and lower portions of flag 84 of jaw member 42. Openings 69a, 69b and, thus, flag 84 are disposed in an offset orientation relative to a longitudinal axis of clevis 41. Flags 86a, 86b of jaw member 44 are positioned such that flag 84 of jaw member 42 is disposed therebetween. Flags 84 and 86b may be disposed in close approximation with one another and, in some configurations, may abut one another (physically abutting or abuttable without any gap-setting structures therebetween). Further, flag 84 extends further proximally into clevis 41 as compared to flags 86a, 86b. More specifically, flags 86a, 86b extends proximally beyond pivot pin 50 (and define a transverse apertures 87 that align with apertures 64a, 85a and receive pivot pin 50 therethrough) but terminate before reaching cam pin 53. Flag 84, on the other hand, extends proximally beyond both pivot pin 50 and cam pin 53 (and defines a transverse aperture 85a for receipt of pivot pin 50 and a transverse cam slot 85b for receipt of cam pin 53).

Flags 86a, 86b defined reduced heights as compared to flag 84 such that flags 86a, 86b are disposed within the interior volume of clevis 41 defined by arms 62, 63, ceiling 65, and floor 66. In particular, flag 86a may be captured within clevis 41 laterally between arm 62 and cutting guide 88a and/or may be captured vertically between ceiling 65 and floor 66. Flag 86b may be captured laterally between arm 63 and flag 84, and/or may be vertically captured via floor 66. Flag 84 may be captured laterally via ceiling 65 and floor 66 of clevis 41 due to the extension of flag 84 vertically into aligned openings 69a, 69b of ceiling 65 and floor 66, respectively. Flag 84 extends into aligned openings 69a, 69b, flag 84 but is not captured vertically, e.g., thereby allowing for pivoting of flag 84 outside the dimensions of clevis 41 as jaw member 42 is pivoted between and/or disposed in the spaced-apart and/or approximated positions.

The above-noted capturing of flags 84 and 86a, 86b, whether laterally and/or vertically, may be complete, e.g., across substantially the entire length and/or height thereof (at least 90%), or may be partial. With respect to partial capture, for example: cutting guide 88a may only extend a portion of the height of flag 86a; and/or opening 69a may communicate with a cut-out 64c defined within arm 63 of clevis 41 along a portion of the length of flag 86b (e.g., wherein cut-out 64c overlaps pivot pin 50 and extends distally therefrom to the distal end of clevis 41).

Wires 98, 99 extend through wire apertures 67a, 67b, which are further offset from the longitudinal axis of clevis 41 as compared to flag 84 (and may be disposed outside flag 86b). In this manner, flag 84 (and, in some configurations, flag 86b) is disposed between the longitudinal axis of clevis 41 and wires 98, 99. Cutter channel 88b and partially-cylindrical cut-out 88c of cutting guide 88a are disposed on the opposite side of the longitudinal axis of clevis 41 as compared to flag 84 with cutter channel 88b and partially-cylindrical cut-out 88c disposed between the longitudinal axis of clevis 41 and flag 86a of jaw member 44.

Turning to FIGS. 12A-12C, another end effector assembly provided in accordance with the present disclosure is shown generally identified by reference numeral 1240. End effector assembly 1240 is similar to and may include any of the features of end effector assembly 40 (FIGS. 1 and 4-11C) detailed above and, thus, only differences between end effector assembly 1240 and end effector assembly 40 (FIGS. 1 and 4-11C) are described in detailed below while similarities are summarily described or omitted entirely.

End effector assembly 1240 includes a pivot pin 1250, a cam pin 1253, a clevis 1241, and first and second jaw members 1242, 1244, respectively, supported by clevis 1241. Clevis 1241 includes a pair of spaced-apart arms 1262, 1263, a ceiling 1265, a floor 1266, first and second wire channels 1267a, 1267b, respectively, defined within one of the arms, e.g., arms 1263, and a cutting guide 1288 defined within one of the arms, e.g., arm 1262. Jaw member 1242 includes a flag 1284 extending into clevis 1241 and operably coupled thereto while jaw member 1244 includes flags 1286a, 1286b extending into and fixedly engaged with clevis 1241.

Ceiling 1265 and floor 1266 of clevis 1241 define aligned openings 1269a, 1269b, respectively, that receive upper and lower portions of flag 1284 of jaw member 1242. Flags 1286a, 1286b of jaw member 1244 are positioned such that flag 1284 of jaw member 1242 is disposed therebetween and in close approximation with flag 1286b. Flags 1284 and 1286a, 1286b extend substantially similar distances proximally into clevis 1241, e.g., any difference therebetween is equal to or less than 10% of the length of the longer flag(s) 1284 or 1286a, 1286b. That is both flag 1284 and flags 1286a, 1286b extend proximally beyond both pivot pin 1250 and cam pin 1253 (and define transverse apertures 1285a, 1287a for receipt of pivot pin 1250 and transverse cam slots 1285b, 1287b for receipt of cam pin 1253).

Flags 1286a, 1286b defined reduced heights as compared to flag 1284 such that flags 1286a, 1286b are disposed vertically between ceiling 1265 and floor 1266 while flag 1284 extends into openings 1269a, 1269b defined within ceiling 1265 and floor 1266, respectively. Flag 1286a may be captured within clevis 1241 laterally between arm 1262 and cutting guide 1288, and/or may be captured vertically between ceiling 1265 and floor 1266. Flag 1286b may be captured laterally between arm 1263 and flag 1284, and/or may be captured vertically via ceiling 1265 and floor 1266. Flag 1284 may be captured laterally via ceiling 1265 and floor 1266 due to the extension of flag 1284 vertically into aligned openings 1269a, 1269b, respectively, but is not vertically captured. The above-noted capturing of flags 1284 and 1286a, 1286b may be complete, e.g., across substantially the entire length and/or height thereof (at least 90%), or may be only partial.

With reference to FIG. 12B, as noted above, flag 1286b may be captured laterally between arm 1263 and flag 1284. More specifically, arm 1263 may define a recess 1289 having a width greater than a thickness of flag 1286b such that flag 1286b is received within recess 1289 without protruding into the volume defined by and extending between aligned openings 1269a, 1269b of ceiling and floor 1265, 1266, respectively. Recess 1289 is bounded vertically via ceiling 1265 and floor 1266. In this configuration, as flag 1286b does not extend into the volume defined by and extending between aligned openings 1269a, 1269b of ceiling and floor 1265, 1266, respectively, the width of aligned openings 1268a, 1268b (and of the volume defined therebetween) may be substantially equal, e.g., within 10%, to a thickness of flag 1284 to inhibit substantial lateral play of flag 1284 within clevis 1241.

Referring to FIGS. 13A-13C, another end effector assembly provided in accordance with the present disclosure is shown generally identified by reference numeral 1340. End effector assembly 1340 is similar to and may include any of the features of end effector assembly 1240 (FIGS. 12A-12C) detailed above and, thus, only differences between end effector assembly 1340 and end effector assembly 1240 (FIGS. 12A-12C) are described in detailed below while similarities are summarily described or omitted entirely.

End effector assembly 1340 includes a pivot pin 1350, a cam pin 1353, a clevis 1341, and first and second jaw members 1342, 1344, respectively, supported by clevis 1341. Clevis 1341 includes a pair of spaced-apart arms 1362, 1363, a ceiling 1365, a floor 1366, first and second wire channels 1367a, 1367b, respectively, defined within one of the arms, e.g., arms 1363, and a cutting guide 1388 defined within one of the arms, e.g., arm 1362. Jaw member 1342 includes a flag 1384 extending into clevis 1341 and operably coupled thereto while jaw member 1344 includes flags 1386a, 1386b extending into and fixedly engaged with clevis 1341.

Flag 1386b may be captured laterally between arm 1363 and flag 1384, and/or may be captured vertically via ceiling 1365 and/or floor 1366. More specifically, arm 1363 may define a recess 1389 having a width less than a thickness of flag 1386b such that, even with flag 1386b fully received within recess 1389, flag 1386b protrudes into the volume defined by and extending between aligned openings 1369a, 1369b of ceiling 1365 and floor 1366. Recess 1389 is bounded vertically via ceiling 1365 and floor 1366. In this configuration, since flag 1386b extends into the volume defined by and extending between aligned openings 1369a, 1369b, the width of aligned openings 1369a, 1369b (and of the volume defined therebetween) is greater than a thickness of flag 1384 to accommodate the protruding portion of flag 1386b in addition to the thickness of flag 1384. However, the width of aligned openings 1369a, 1369b (and of the volume defined therebetween) minus the protruding width portion of flag 1386b (which occupies a portion of the volume defined between aligned openings 1369a, 1369b) may be substantially equal, e.g., within 10%, to the thickness of flag 1384 to inhibit substantial lateral play of flag 1384 within clevis 1341.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. An end effector assembly of a surgical instrument, comprising:
   a clevis including a proximal body, first and second arms extending distally from the proximal body in spaced-apart relation relative to one another arms, and at least one of: a ceiling extending at least partially between upper portions of the first and second arms, or a floor extending at least partially between lower portion of the first and second arms;
   a pivot pin extending transversely at least partially between the first and second arms of the clevis;

a cam pin extending transversely at least partially between the first and second arms of the clevis, the cam pin positioned proximally of the pivot pin;

a first jaw member including a proximal extension portion disposed at least partially within the clevis and a distal jaw body extending distally from the clevis, the proximal extension portion including a first flag disposed between the first and second arms of the clevis and extending vertically at least partially through openings defined within the ceiling and floor to inhibit lateral motion thereof, the first flag defining a pivot aperture through which the pivot pin extends and a cam slot through which the cam pin extends; and a second jaw member including a proximal extension portion disposed at least partially within the clevis and a distal jaw body extending distally from the clevis, the proximal extension portion including second and third flags disposed between the first and second arms of the clevis in spaced-apart relative to one another and between the ceiling and the floor, the second and third flags fixedly engaged to the clevis, the second and third flags defining pivot apertures through which the pivot pin extends, wherein proximal ends of the second and third flags terminate distally of the cam pin, wherein the first flag is disposed between the second and third flags in an offset position such that the first flag is disposed closer to the third flag than the second flag, and a cam block coupled to the cam pin and configured to slide through the clevis to thereby move the cam pin through the cam slot, the cam block having first, second, and third outwardly-facing sides and received within a substantially complementary cavity within the clevis defined by first, second, and third inwardly-facing sides configured to guide the first, second, and third outwardly-facing sides of the cam block, respectively, the first inwardly-facing side defined at least partially by the ceiling of the clevis or the floor of the clevis, the second inwardly-facing side defined at least partially by one of the first or second arms of the clevis, and the third inwardly-facing side defined at least partially by the first flag.

2. The end effector assembly according to claim 1, wherein the third flag is captured between the second arm of the clevis and the first flag.

3. The end effector assembly according to claim 1, wherein the clevis further includes a cutter guide disposed between the first and second arms.

4. The end effector assembly according to claim 3, wherein the cutter guide defines a first portion configured to slidably receive a cutting element, and a second portion configured to slidably receive a drive structure associated with the cutting element.

5. The end effector assembly according to claim 3, wherein the second flag is captured between the first arm of the clevis and the cutter guide.

6. The end effector assembly according to claim 1, wherein sliding of the cam block through the clevis slides the cam pin through the cam slot to pivot the distal jaw body of the first jaw member relative to the distal jaw body of the second jaw member between a spaced-apart position and an approximated position.

7. The end effector assembly according to claim 1, wherein, in a distal-most position, the cam block partially surrounds the pivot pin.

8. The end effector assembly according to claim 1, wherein the second arm of the clevis defines first and second wire channels extending therethrough outwardly of the third flag.

9. The end effector assembly according to claim 1, wherein the first flag defines a height greater than heights of each of the second and third flags.

10. The end effector assembly according to claim 1, wherein the cam block further includes a fourth outwardly-facing side, and wherein the other of the ceiling or the floor defines a fourth inwardly-facing side of the substantially complementary cavity of the clevis to guide the fourth outwardly-facing side of the cam block.

11. An end effector assembly of a surgical instrument, comprising:

a clevis including a proximal body, first and second arms extending distally from the proximal body in spaced-apart relation relative to one another arms, a ceiling extending at least partially between upper portions of the first and second arms, and a floor extending at least partially between lower portion of the first and second arms wherein the first and second arms of the clevis define opposing inwardly-facing surfaces positioned distally of the proximal body;

a pivot pin extending transversely at least partially between the first and second arms of the clevis;

a cam pin extending transversely at least partially between the first and second arms of the clevis;

a first jaw member including a proximal extension portion disposed at least partially within the clevis and a distal jaw body extending distally from the clevis, the proximal extension portion including a first flag disposed between the first and second arms of the clevis and extending vertically at least partially through openings defined within the ceiling and floor, the first flag defining a pivot aperture through which the pivot pin extends and a cam slot through which the cam pin extends; and a second jaw member including a proximal extension portion disposed at least partially within the clevis and a distal jaw body extending distally from the clevis, the proximal extension portion including second and third flags disposed between the first and second arms of the clevis in spaced-apart relative to one another and between the ceiling and the floor, the second and third flags engaged to the clevis in a stationary position relative to the clevis, the second and third flags defining pivot apertures through which the pivot pin extends and cam slots through which the cam pin extends, the third flag at least partially disposed within a recess defined within the inwardly facing surface of the second arm of the clevis, wherein the first flag is disposed between the second and third flags in an offset position such that the first flag is disposed closer to the third flag than the second flag, and wherein the first flag, the second flag, and one of the ceiling or the floor of the clevis define first, second, and third inwardly-facing sides, respectively, of a cavity configured to receive a cam block supporting the cam pin thereon such that the first, second, and third inwardly-facing sides guide respective first, second, and third outwardly-facing sides of the cam block.

12. The end effector assembly according to claim 11, wherein the third flag is fully disposed within the recess and wherein the first flag extends vertically at least partially through the openings defined within the ceiling and floor such that the ceiling and floor inhibit lateral motion of the first flag.

13. The end effector assembly according to claim 11, wherein the third flag is partially disposed within the recess and a portion thereof protrudes inwardly therefrom, and wherein the first flag extends vertically at least partially through the openings defined within the ceiling and floor, the protruding portion of the third flag together with the ceiling and floor inhibiting lateral motion of the first flag.

14. The end effector assembly according to claim 11, wherein the clevis further includes a cutter guide disposed between the first and second arms.

15. The end effector assembly according to claim 14, wherein the second flag is captured between the first arm of the clevis and the cutter guide.

16. The end effector assembly according to claim 14, wherein the cutter guide defines a first portion configured to slidably receive a cutting element, and a second portion configured to slidably receive a drive structure associated with the cutting element.

17. The end effector assembly according to claim 11, wherein sliding of the cam block through the cavity slides the cam pin through the cam slot of the first flag and the cam slots of the second and third flags to pivot the distal jaw body of the first jaw member relative to the distal jaw body of the second jaw member between a spaced-apart position and an approximated position.

18. The end effector assembly according to claim 11, wherein the second arm of the clevis defines first and second wire channels extending therethrough outwardly of the third flag.

19. The end effector assembly according to claim 11, wherein the first flag defines a height greater than heights of each of the second and third flags.

20. The end effector assembly according to claim 11, wherein the other of the ceiling or the floor of the clevis defines a fourth inwardly-facing side of the cavity to guide a fourth outwardly-facing side of the cam block.

* * * * *